United States Patent [19]

Purser

[11] Patent Number: 5,621,209
[45] Date of Patent: Apr. 15, 1997

[54] ATTOMOLE DETECTOR

[75] Inventor: Kenneth H. Purser, Lexington, Mass.

[73] Assignee: High Voltage Engineering Europa B.V., Netherlands

[21] Appl. No.: 420,192

[22] Filed: Apr. 10, 1995

[51] Int. Cl.$^6$ ............................ H01J 49/00; B01D 59/44
[52] U.S. Cl. ............................................ 250/296; 250/281
[58] Field of Search ................................. 250/281, 282, 250/296, 297

[56]  References Cited

U.S. PATENT DOCUMENTS

| | | | |
|---|---|---|---|
| 4,037,100 | 7/1972 | Purser | 250/281 |
| 4,489,237 | 12/1984 | Litherland et al. | 250/287 |
| 4,866,267 | 9/1989 | Matsuda | 250/296 |
| 4,973,841 | 11/1990 | Purser | 250/282 |
| 5,013,923 | 5/1991 | Litherland et al. | 250/296 |
| 5,237,174 | 4/1993 | Purser | 250/296 |
| 5,438,194 | 8/1995 | Koudijs | 250/288 |

*Primary Examiner*—Bruce C. Anderson
*Attorney, Agent, or Firm*—Nields & Lemack

[57] ABSTRACT

This invention relates to the detection of the radioisiotope carbon-14 using Accelerator Mass Spectrometry (AMS). This invention has particular relevance to the fields of attomole level ($10^{-18}$ molar) tracking of chemicals in biomedicine and the environment, the testing of new classes of medical drugs, the whereabouts of chemotherapy agents within cancer patients, the elimination of the need to store and dispose of low-level carbon-14 nuclear waste and neutron exposure monitoring around nuclear reactors.

13 Claims, 4 Drawing Sheets

ATTOMOLE DETECTOR

BACKGROUND OF THE INVENTION

1. Field of the Invention

This invention relates to the detection of the radioisotope carbon-14 using Accelerator Mass Spectrometry (AMS). Although limitations in scope are not intended, this invention has particular relevance to the fields of attomole ($10^{-18}$ molar) detection of chemicals. Also neutron exposure monitoring around nuclear reactor and weapons production sites.

2. Description of Prior Art

Attomole and even zeptomole ($10^{-21}$ mole) detection are becoming important in modern biochemistry, particularly with the introduction of separation procedures such as Capillary Electrophoresis, where the yield of a specific fraction of the defined material may be only picomoles. Carbon-14 is important as a label for tracking such small quantities. It has a unique detection signature and can be incorporated into specific ligands of an organic compound without modifying the compound's chemical behavior. However, historically, carbon-14's half life is so long that when decay methods are used for detection, attomole ($10^{-18}$ mole) sensitivities are not available; the detection efficiency is such that it is barely possible to detect five femtomoles of carbon-14 in an idea sample.

During the last fifteen years the sensitivity for detecting carbon-14 labels has been enhanced by many orders of magnitude using the detection technique of accelerator mass spectrometry (AMS). Using AMS, individual carbon-14 atoms are detected directly using mass spectrometric methods rather than waiting for the associated radioactive decay. In practice, seven orders of magnitude increase in sensitivity become available. The principles of AMS have been described in detail by a number of authors including, for example U.S. Pat. No. 4,037,100 to K. H. Purser; K. H. Purser, H. E. Gove and A. E. Litherland, "Ultra-sensitive Particle Identification Systems Based Upon Electrostatic Accelerators", *Nuclear Instruments and Methods*, Volume 162, page 637 (1979), and by D. Elmore and F. M. Phillips "Accelerator Mass Spectrometry" in *Science, Volume* 236, page 543, (1987).

Examples of the potential applications of AMS detection of carbon-14 labels in biomedicine have been reviewed by J. S. Felton, K. W. Turteltaub, J. S. Vogel, R. Baithorne, B. L. Gledhill, J. R. Southon, M. W. Caffee, R. C. Finkel, D. E. Nelson, I. D. Proctor and J. C. Davis in *Nuclear Instruments and Methods in Physics Research*, Volume B52, page 517 (1990). These workers have demonstrated chemical detection limits of quantities as small as 300 zeptomoles. The high efficiency of detection is such that attomole quantities of molecules enriched in $^{14}C$ to only 100 to 1000 times the activity of natural biological carbon, can provide clear signals.

Apart from the new frontiers that become available in biomedicine, using AMS, an important social consequence is that disposal becomes trivial for carbon-14 waste generated by such low-level experiments. Incineration of waste followed by stack gas dilution with "dead" carbon dioxide (from the simultaneous burning of ordinary fuel oil or dilution with tank $CO_2$) can produce a released activity of carbon-14 that is at or even below the natural level of carbon-14 in the atmosphere.

3. Existing Size Limitation

Referring to FIG. 1, it can be seen that AMS is a type of tandem mass spectrometry in which the two mass spectrometers are separated by an electrostatic accelerator that provides a kinetic energy gain from the kilo-electron-volt energies (keV) used in classical mass spectroscopy to million-electron-volt energies (MeV). At MeV energies, nuclear detection techniques can be applied for counting and identifying individual ions, often with high efficiency and precision. The accelerator also effects a conversion from negative to multiply charged positive ions.

It is known that all molecular interferences can be eliminated by the Coulomb explosion process if carbon-14 atoms in charge states $3^+$ or above are selected by the second analysis stage of the instrument shown in FIG. 1. Hoffman, et al. in *Nuclear Instruments and Methods*, Volume B5, page 254, (1984) shows that to achieve a maximum yield of $^{14}C^{3+}$ ions (the minimum positive ion charge state that guarantees molecule dissociation for the interfering molecular species relevant to carbon-14 detection), tandem voltages of 2–3 million volts are essential. Thus, the necessity for insulating such voltages sets the scale of size for the whole AMS instrument. Tandems employing terminal voltages of 3 MV are not small and their size tends to preclude installation within conventional biomedical or chemical laboratories.

As a method of avoiding the above 3+constraint, K. H. Purser in U.S. Pat. No. 4,973,841 describes a more compact apparatus based upon stripping to the $2^+$ charge state during the acceleration phase. To guarantee molecular background elimination, a second stripping is made to $3^+$ before final analysis and detection. At an energy of 800 keV, more than 50% of the carbon ions leave a foil in the $2^+$ charge state so that in this part of the apparatus the efficiency is acceptable. However, the succeeding requirement of U.S. Pat. No. 4,973,841 for a second charge changing transition to the $3^+$ charge state, reduces the detection efficiency by at least a factor of two below that of conventional 3 MV machines.

SUMMARY OF THE INVENTION

The present invention comprehends a compact and economical apparatus that carries out the task of efficiently detecting carbon-14 atoms using a tandem accelerator with terminal voltages of 800 kV or less. For measurements where a high background level is acceptable a single foil can be used. However, for measurements requiring low backgrounds a novel stripping arrangement consisting of two closely spaced thin carbon foils in the high voltage terminal of the tandem is used to charge change negative carbon-14 ions to the 2+ charge state. The requirement of Purser in U.S. Pat. No. 4,973,841 for a second charge exchange from $2^+$ to $3^+$ to guarantee molecular elimination is avoided by the use of the above two thin foils that are separated by a few millimeters. Thus, the detection efficiency is high and may be even greater than that demonstrated by conventional $^{14}C^{3+}$ AMS systems reported by K. H. Purser, in the magazine, *Radiocarbon*, Volume 34, page 458, (1992).

BRIEF DESCRIPTION OF THE DRAWINGS

Operation of the invention may best be understood from the following detailed description thereof, having reference to the accompanying drawings, in which.

DESCRIPTION OF THE PREFERRED EMBODIMENT

Figure 2:
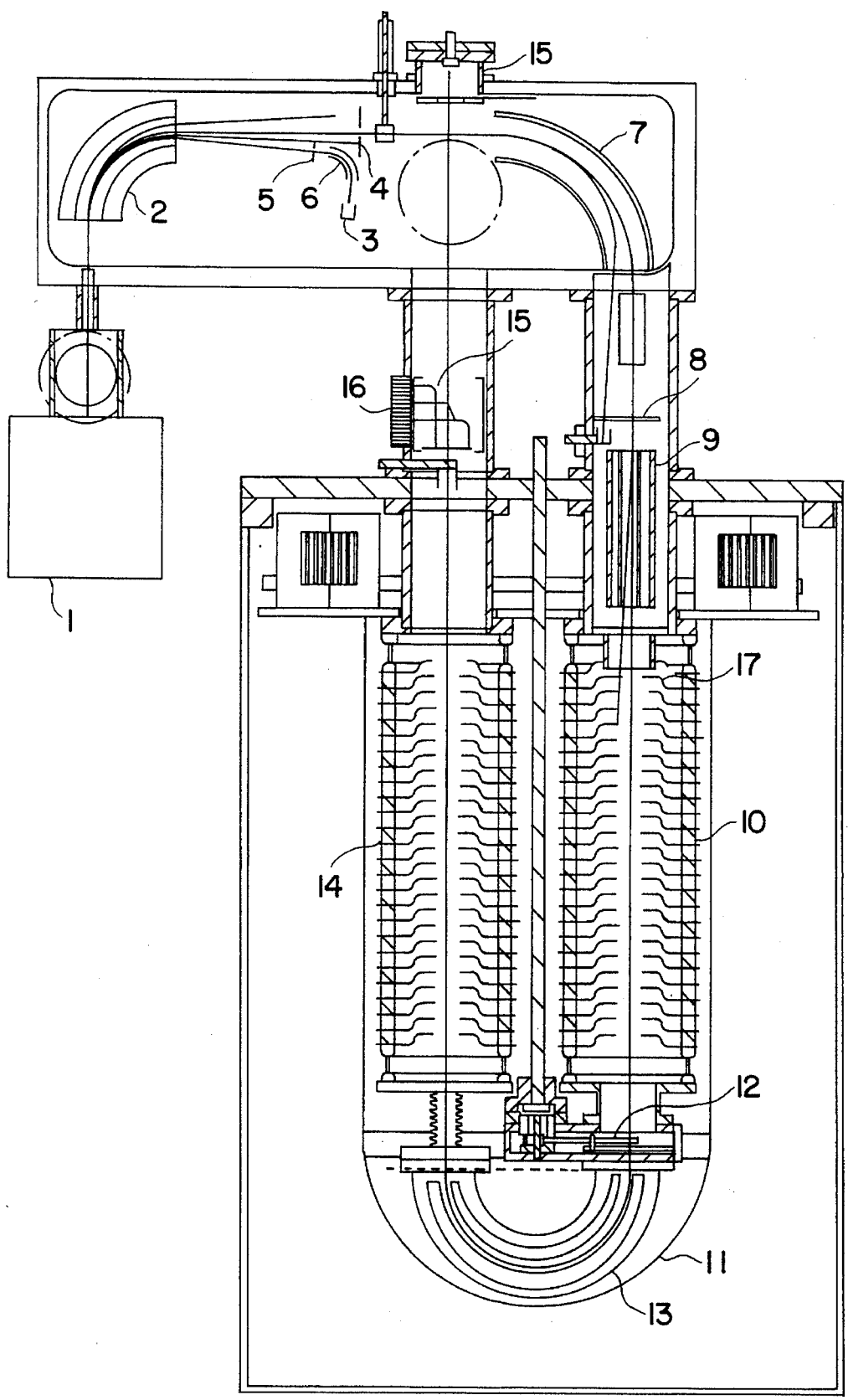
FIG. 2 is a drawing of the Preferred Embodiment.

Referring to the drawings and first to FIG. 2 thereof, therein is shown a schematic of the present invention.

The following section summarizes the operation of the complete invention. Negative ions are extracted from the source (1) with an energy that typically might be 30 keV. These ions are then mass analyzed to remove almost all unwanted particles using a mass spectrometer that presents at its output spearated beams of masses 12, 13 and 14 ions, rejecting all others. The mass-14 particles leaving this spectrometer are further accelerated to a high voltage terminal maintained at a d.c. electrical potential of about 800 kV, where they arrive with an energy of approximately 830 keV. At the high voltage terminal the negative ions are stripped of electrons and the molecules are fragmented into lighter components. Ions having an energy of 830 keV and a charge state of 2+ are selected by a 180-degree electrostatic deflector that also performs the function of removing all molecular fragments. The selected 2+ ions are accelerated a second time, back to ground potential where they arrive with an energy of approximately 2430 keV. The particles are stopped in a particle detector, similar to that described in the above article by Purser, Gore and Litherland, to provide further discrimination between bona-fide C-14 events and residual backgrounds.

1. Kinematic Constraints

It is known to those skilled in the art of ion beams using magnetic and electric fields depends linearly or in product form upon the two variables, E/q and M/q:

Magnetic Deflection: $(M_q \times E_q) = K_1$

Electric Field Deflection: $(E_q) = K_2$

Cyclotron Resonance: $(M_q) = K_3$

Velocity Filter: $(M_q/E_q) = K_4$

Here, M is the mass of the ion, E is the energy and q (multiplied by e, the electronic charge) is the ion charge. The constants, $K_1$–$K_4$, are constants of the deflecting field geometry, and the cyclotron frequency.

Figure 1:
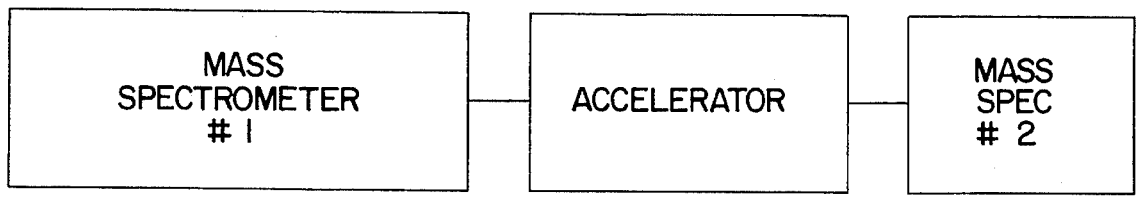
FIG. 1 shows schematically the principles of AMS.
Figure 3:
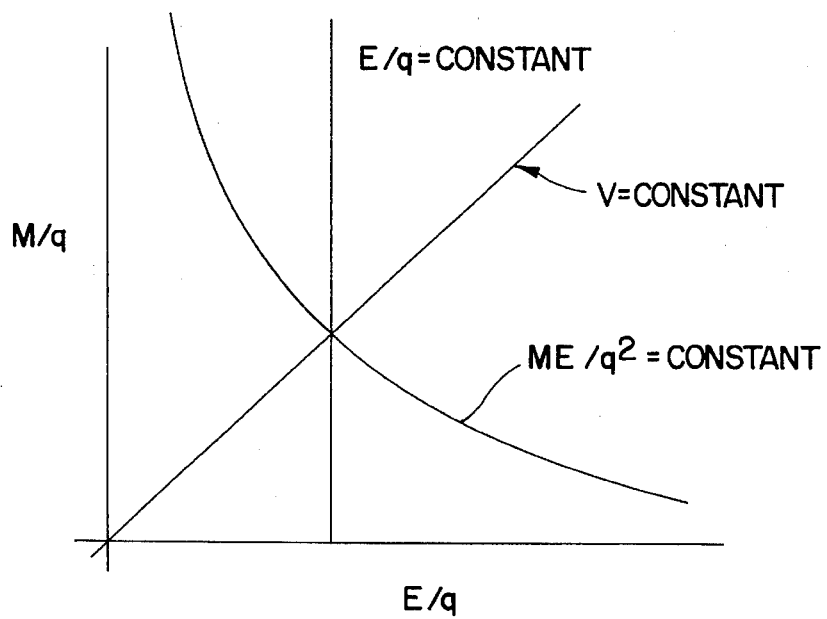
FIG. 3 shows the constraints of electric and magnetic fields in (E/q, M/q) space.

The effects of these four constraints of the mass filter can best be demonstrated by reference to FIG. 3 where the variable M/q is plotted against E/q. Several loci can be drawn to represent the constraints imposed by sector magnetic fields, electric fields and a velocity filter (a Wien filter). The hyperbolic band shows the parameters of particle that can be transmitted without loss through a single sector of magnetic field. The vertical band defines those particles that will pass unattenuated through an electric sector, and the straight line through the origin defines the acceptance of a velocity filter (Wien filter).

Because kinematic constraints can be independently imposed on the transmission of individual particles, any two can be used to define a point in the $(M_q, E_q)$ plane. However, it should be mentioned that gas sccattering and charge changing introduced backgrounds that can only be eliminated by adding more stages. Only particles with these coordinates can be transmitted. Also, a solution of this type is not unique; a common multiple or sub-multiples of each of the variables, M, E, and q, represent mass ambiguities that cannot be distinguished by electric and magnetic fields alone. In the present instrument, the ion $^7Li^+$, derived from the $^7Li_2^-$ dimer, falls into this class. However, experiment indicates that this background is not observable if modest care is take during sample preparation.

Referring again to FIG. 3, it can be seen that because the masses of all background particles are separated from the wanted carbon-14 by at least one mass unit, the resolution in each of the filtering stages of the above mass spectrometer need not be high to achieve excellent background discrimination. Generously sized defining apertures can be used to permit high transmission efficiency for the wanted carbon-14 particles.

2. The Mass Spectrometer

In the following paragraphs (I) through (III), three examples of filter stages are described. Coupled sequentially together the combination achieves the rejection factor necessary for the preferred embodiment.

(I) The first filter stage (momentum filter)

Referring again to FIG. 2, negative ions leave the source, (1), with an energy that is typically 30 keV. The said ions are directed through a double focusing 90° magnetic analyzer, (2). Ions having similar magnetic rigidity to that of 30 keV $^{14}C^-$ pass through the defining aperture, (4).

Ions having a magnetic rigidity equal to that of 30 keV carbon-12 are directed through the monitoring aperture, (5) and into a faraday cup, (3), to supply the data needed for providing $^{14}C/^{12}C$ ratio information. Because there may also be a substantial contribution at aperture, 5, from $^{16}O^-$ ions having an energy of 22.5 keV (12/16×30 keV), an electrostatic deflector, (6), is included. Any $^{16}O^{31}$ ions will be deflected on a trajectory having a smaller radius of curvature than $^{12}C^-$ and strike the inner electrode.

The majority of those background particles that pass through the mass-14 channel aperture, (4), have identical magnetic rigidity to $^{14}C^-$ ions. These include (i) the mass-14 molecules $^{12}CH_2^-$, $^{13}CH^-$, and $^7Li_2^-$; (ii) heavier ions that have spent some time as a neutral in the extraction region of the source so their energy is lower; (iii) if a gas exchange source is used, lighter ions that have acquired additional energy by spending some time in the extraction region as a doubly charged particle. Fortunately, the mass-14 isobar $^{14}N^-$ will not be present as $N^-$ is known to be unstable against spontaneous dissociation.

(II) The Second Filter Stage (Energy Filter)

Other than mass-14 molecules, most of the unwanted background particles passing through said defining aperture, (4), will not have an energy of 30 keV and thus will be eliminated at the energy defining aperture, (8), that follows the electrostatic deflection, (7). It should be emphasized that even following this second stage of filtering where a single point has been defined in the E/q, M/q plane shown in FIG. 3, background elimination may not be adequate because of the high cross section for charge changing in the residual gas.

(III). The Third Filter Stage (Velocity Filter)

Depending upon the efficiency of the first two stages of the mass filter and the cleanliness of the ion source, a third stage of selection may be needed to eliminate residual background particles. Those skilled in the art will recognize that several options are available for this third stage of elimination of unwanted masses. In the preferred embodiment this third filter comprises a region of crossed uniform electric and magnetic fields, (9), arranged in the form of a conventional Wien Filter. The effect is that only those particles having the specified velocity are retained on the acceleration axis. Other background particles will be eliminated within the negative ion acceleration tube.

3. The First Acceleration Stage and Molecule Destruction

The mass-14 ions that exit the above mass spectrometer stages are accelerated by a uniform field acceleration region, (10), to a high voltage terminal, (11), maintained at a voltage of 800 kV. While 800 kV is a satisfactory compromise between transmission efficiency, size and expense, it will be recognized by those skilled in the art that higher or lower terminal voltages can be used also.

After arriving at the terminal, the previously mass analyzed particles pass through a pair of thin carbon foils, (12), where electrons are stripped from carbon-14 atoms and where background molecules are completely dissociated. On leaving the foil pair, approximately 50% of the $^{14}C$ particles are in the $2^+$ charge state.

While single foil operation is possible during those occasions when low backgrounds are not needed, two thin foils are needed when the backgrounds must be minimized. The underlying reason underlying the need for two foils is that on rare occasions the molecular fragments from breakup of the $^{12}CH_2$ background are aligned along the trajectory allowing their spatial configuration to be maintained throughout the $10^{-15}$ second passage through the foil. Thus, when they leave the stripping foil the possibility exists for the molecule to reform and re-emerge as $^{12}CH_2^{++}$.

4. The Terminal Electrostatic Analyzer

In the preferred embodiment, the $^{14}C$ in all charge states, plus all of the components from the fragmented molecules, enter a semicircular electric deflector, (13). When $^{13}CH^-$ molecules dissociate in the foil, the residual $^{13}C^{++}$ have an energy of 13/14 of 800 keV or 743 keV. These ions are deflected to a point approximately 21 mm away from the defining aperture at the exit from the 180° spherical electrostatic analyzer and so are rejected before the following second stage of high energy acceleration, (16).

At this stage of background reduction, the residual particles leaving the 180° electrostatic deflector are $^{14}C^{++}$ together with a relatively few atomic particles that have managed to acquire the correct energy and charge state to be transmitted around the 180° deflector.

Those skilled in the art will recognize that several well known techniques can be used to discriminate against such residual background particles. Some have been discussed in detail in the above paper by Purser, Gove and Litherland. They include in combination time-of-flight discrimination, magnetic deflection and the use of a detector that measures both the energy and the rate of energy loss for each arriving particle.

5. Second Tandem Acceleration

The second stage of tandem acceleration, (14), returns the ions to ground where they exit the acceleration section with an energy $E_f$:

$$E_f = E_{inj} - \Delta E_f + V_t(1+q)$$

For the case where $E_{inj}$ (injection energy)=30 keV $\Delta E_f$ (energy loss in two foils)=9 keV $V_t$ (terminal voltage)=800 keV q=2

$E_f$=2421 keV

6. Final Time-of-Flight

In the preferred embodiment, the final separation, (15), is a time-of-flight region in which the wanted carbon-14 ions have a flight time of approximately 110 nanoseconds. It will be recognized by those skilled in the art that such identification systems are routine and can provide sub-nanosecond timing resolution. A clear distinction is possible between $^{14}C^{++}$ and all other masses. Half-energy $^7Li^+$ ions that have left the source as the dimer $^7Li_2^-$ and dissociate in the terminal foil to $^7Li^+$ enter this stage with the same velocity. If necessary, $^7Li^+$ can be distinguished from $^{14}C^{++}$ on the basis of smaller dE/dx losses in a 20 µg/cm² START foil.

7. Final Detector

An important feature of the invention described here is that the final energy of the ions is sufficiently high that they can be stopped in an appropriate energy sensitive detector making possible an accurate measurement of the final kinetic energy of the particle and its rate of energy loss. The importance of this final measurement is that it makes possible an unambiguous identification of the C-14 events and separates them clearly from any $^{13}C$ or $^{12}C$ fragments which may have been scattered from the walls of the vacuum system into the detector. In addition, any $^{14}N$ fragments which may have originated from hydride molecules in the ion source can be uniquely identified.

10 Synnart of Background Attenuation

Figure 4:
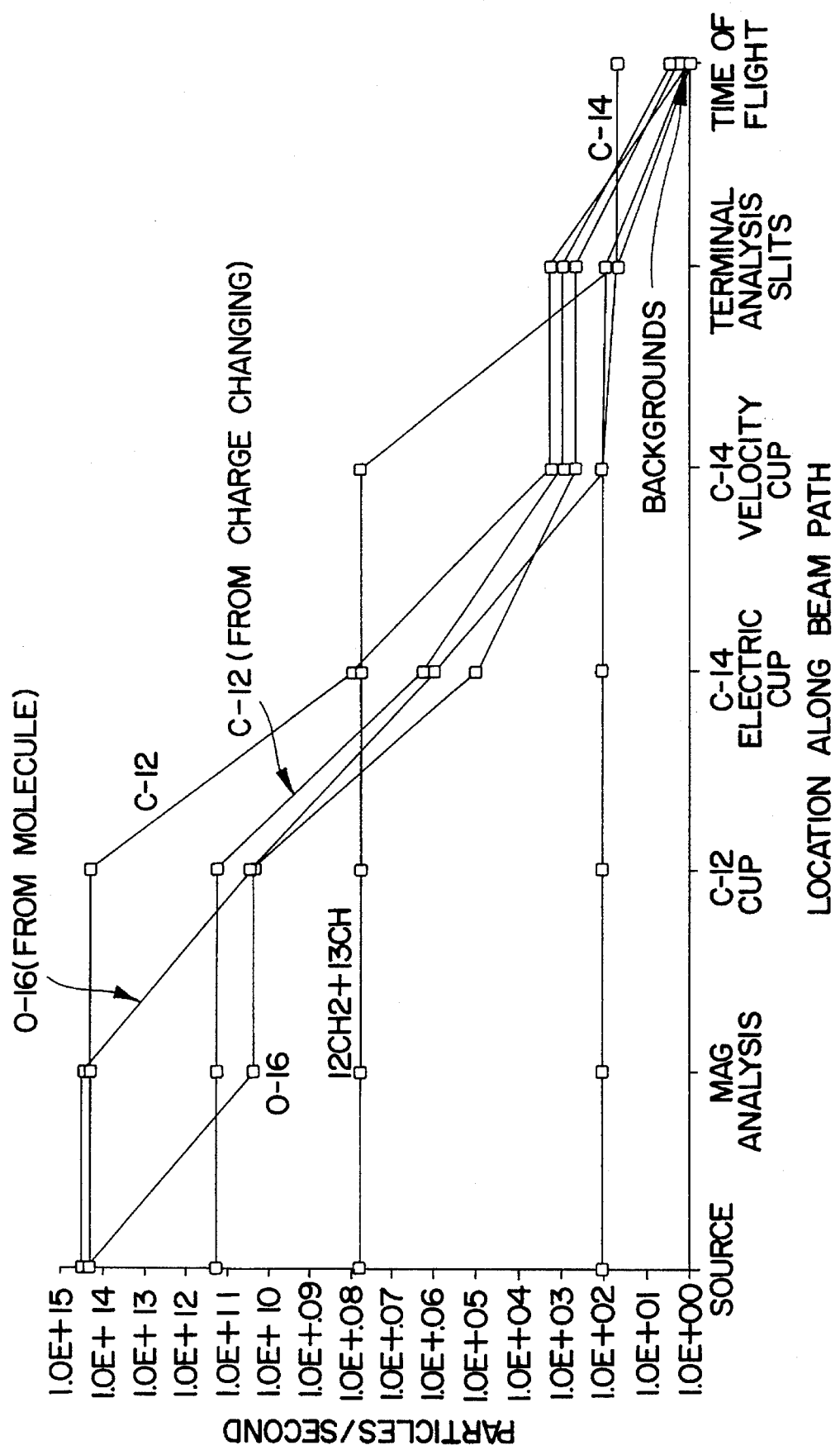
FIG. 4 shows the attenuation of different background components.

FIG. 4 summarizes the expected attenuation of background ion beams throughout the preferred embodiment.

B. Instrument Optics

1. Focusing Introduced by Magnetic Analyzer

Referring again to FIG. 2, it can be seen that the first element in the optical train is a double focusing magnetic deflector, (2). In the preferred embodiment, this element is a uniform field permanent magnet with double focusing being achieved by pole edge rotation. The current in the $^{12}C$ beam needed for $^{14}C/^{12}C$ normalization, is obtained from a suitably suppressed Faraday Cup, (3).

Figure 5:
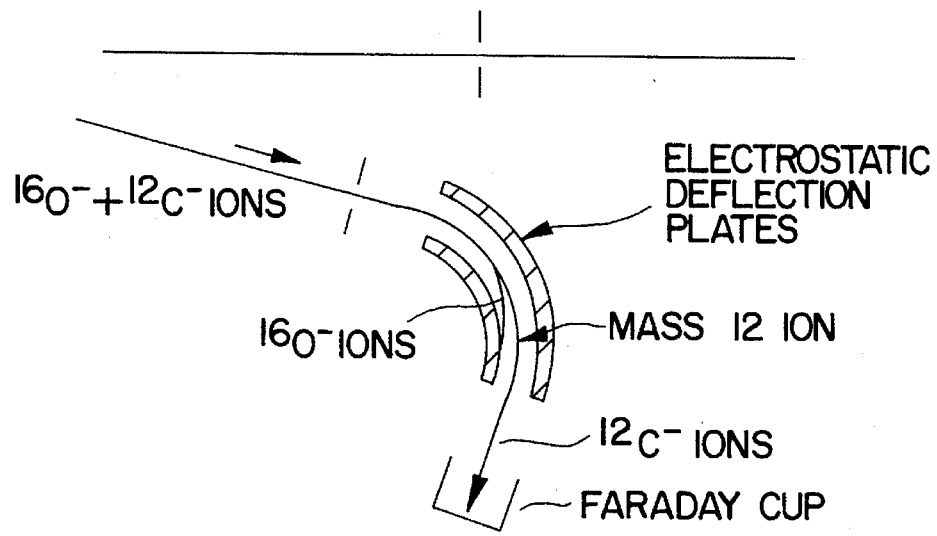
FIG. 5 shows the electrostatic analyzer needed to remove Mass-12 backgrounds.

Carbon dioxide gas is the material of choice for source operation in a biomedical instrument. Thus, it is likely that there will be substantial contributions to the $^{12}C^-$ currents from unwanted $^{16}O^-$ ions having the same magnetic rigidity. These unwanted $^{16}O^-$ ions are eliminated by adding a small radius electrostatic deflector, (6), immediately following the mass-12 defining slits, (5). A schematic diagram of this suppresser is shown in FIG. 5.

2. Non-Dispersive Geometry.

The spherical electrostatic deflector, (7), focuses the two-dimensional beam waist at the defining aperture, (4), to a second waist at the aperture, (8). In the preferred embodiment, the equilibrium radius of curvature of this electrostatic deflector is equal to that of the analysis magnet, (2). This equality causes the combinations of the first and second analysis stages to be point-to-point non-dispersive. In other words, small changes in the energy of ions leaving the source do not cause shifts in the beam position at aperture (8). Non-dispersion leads to stable transmission performance.

3. Gridded Lens Focusing

In the preferred embodiment, the object point for the focusing optics of the negative ion acceleration tube is the defining aperture, (8). Only weak focusing is needed in the first acceleration section as it is desirable that a parallel beam of particles exit this acceleration tube. To provide adjustability in lens strength and also to make the tube entrance lens sufficiently weak, a gridded lens, (17), is included in the preferred embodiment to terminate the electric field and provide variable lens strength. The usefulness of gridded lenses for terminating accelerator fields has been described by K. H. Purser in U.S. Pat. No. 3,423,684 (1969).

4. Terminal Electrostatic Deflector

A spherical electrostatic deflector, (13), within the terminal directs the ions into the positive ion acceleration tube, (14). Details of such deflectors have been discussed by H. Wollnik in "Focusing of Charged Particles" (page 163, edited by A. Septier, Academic Press (1967). By using the above described gridded lens at the entrance to the negative ion acceleration tubes, (17), it is possible to focus the wanted ions to a waist at the center of the deflector (13), rather than to the center of the preceding stripping foils. The optical arrangement becomes point-to-point non-dispersive against small changes in the beam energy and in the spherical electric deflecting fields.

Figure 6:
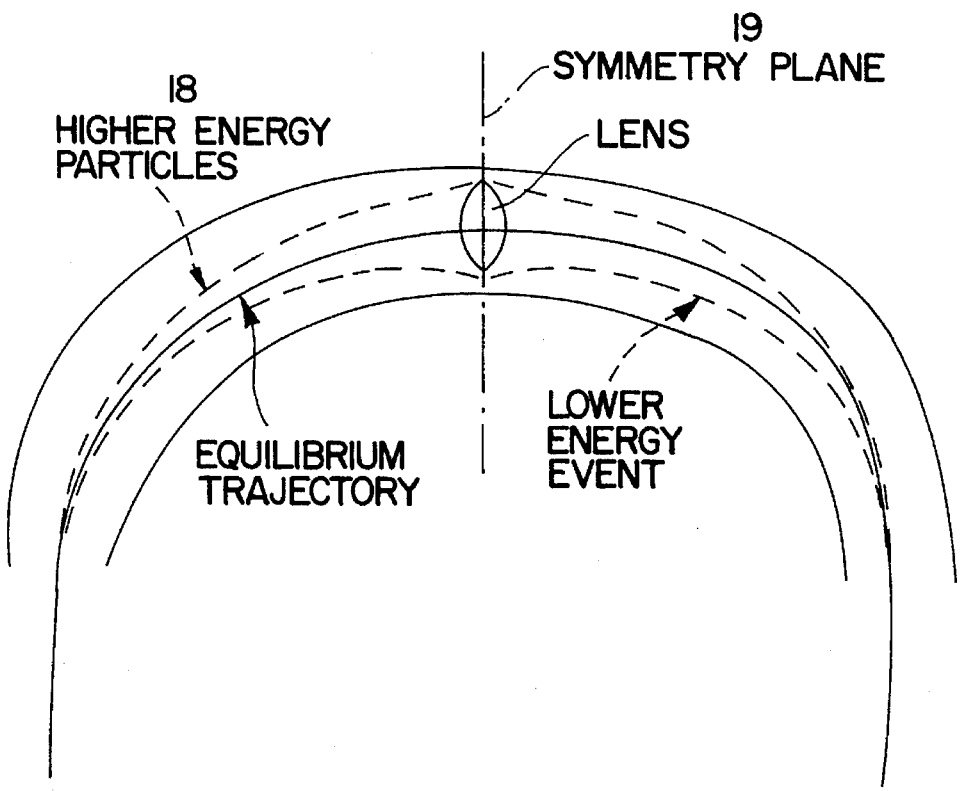
FIG. 6 shows the manner in which a positive lens introduced at the center of the terminal electrotatic deflector produces stable operation.

The above non-dispersive characteristic can be extended by strengthening the positive focusing at the central point in the deflection plane, as shown in FIG. 6. When the energy of the ions increases slightly, the higher energy trajectory, (18), moves away from the equilibrium trajectory and is bent by the focusing lens action so that the entry and exit angles about the mirror plane, (19), become equal. The reverse is true for trajectories having reduced energy. Thus, if an appropriate lens strength is built into the basic deflector design the incoming and outgoing trajectories will be symmetrical about the mirror plane, (19). Those skilled in the art will recognize that the appropriate quadrupole shapes can be carved into the plates during manufacture. With this addition, the direction and location of the exiting ion beams from the deflector remain stable against small changes in foil thickness, ion energy and electric fields within the deflector. This leads to transmission characteristics for the complete instrument that are inherently stable against most fluctuations.

The voltage needed for the electrostatic deflector is derived from the terminal potential. The current which flows down the resistor chain is directly proportional to the energy of the ions when they arrive at the entrance to the foil. Thus, if the potential to drive the electrostatic deflector is derived from a suitable section of this resistor chain, the electric deflection field will scale linearly with the energy of the ions when they reach the high voltage terminal. Because the deflection voltages are derived from a simple resistor divider arrangement, the voltage stability of the high voltage terminal does not need to be highly precise which guarantees good particle transmission at all times.

5. Positive Acceleration Tube Focusing

The final focusing element in the instrument is the positive ion acceleration tube, (14).

The optical properties of this element must focus the ions leaving the waist at the center of the 180° deflector to a beam waist at the START detector, (15). Because the energy of the ions is high compared to field gradient, the entrance lens to the accelerator tube is comparatively weak (focal length~1.3 meters). Thus, by itself, the focal properties of the positive ion acceleration tube are not strong enough to produce a beam waist at the START foil of the final time-of-flight detector.

It will be clear to those skilled in the art that the necessary additional focusing can be introduced in several ways. In the preferred embodiment, the teachings of Enge in U.S. Pat. No. 3,629,576, have been applied to introduce quadrupole components to the acceleration fields along the length of the positive ion acceleration tube. This can be done by shaping the central region of each electrode of what would normally be a plane, into the shape of a saddle. Each electrode is shaped so that at a given radial distance from the tube axis the displacement from a plane electrode varies in a sinusoidal fashion with angle around the axis and with an amplitude that is proportional to the square of the radial distance.

6. Secondary Particle Suppression

Eliminating any micro discharge-generated particles is critical to avoiding detector overloads. The parts of the quadrupole described above, have radial components that also serve to direct into the tube electrodes, secondary particles that might be generated during micro-discharges. As additional protection in the preferred embodiment, the normal to each electrode plane is tilted at about 10° to the central axis of the tube according to the teachings of R. J. Van de Graaff, P. H. Rose and A. B. Wittkower in *Nature*, Volume 195, page 1293 (1962) and of W. D. Allen in U.S. Pat. No. 3,304,454 (1962). In the preferred embodiment, this tilting vector is arranged in two groups that divide the tube into two sections having equal ion transit time. Thus, the ions that are deviated in the first section of the tube are returned to a parallel direction in the second section. Transverse magnetic fields of magnitude 50–100 gauss are also included at all points along the beam line. This field causes any secondary electrons to be intercepted by the tube electrodes while their energies are low, minimizing the production of secondary bremsstrahlung and characteristic X-rays.

I claim:

1. An apparatus for measuring the amount of C-14 in a sample comprising the following components:

a source which ionizes the sample to form a negative ion beam of known energy;

a first apertured member having a first aperture;

a mass analyzer which deflects said negative ion beam and directs it onto said first apertured member so that only mass-14 particles having the above known energy pass through said first aperture;

a first high voltage electrostatic acceleration tube which accelerates said selected mass-14 negative ions to an energy E of the order of 800 keV along a first acceleration axis;

a foil stripper through which said accelerated mass-14 negative ions are directed and which removes three electrons from a fraction of said negative ions to form doubly-charged positive ions;

a second apertured member having a second aperture;

a deflector which deflects said doubly-charged positive ions through approximately 180° using an electrostatic deflecting field that directs the deflected beam onto said second apertured member so that only said particles in the doubly charged positive ion state and having an energy E pass through said second aperture;

a second high-voltage electrostatic acceleration tube adapted to accelerate said doubly charged positive ions passing through said second aperture to a final energy of about 3E along the second accelerator axis; and a detector which identifies individually said doubly charged positive ions as they leave said second acceleration tube.

2. The apparatus of claim 1 wherein the mass analyzer consists of the following components:

a magnetic deflector that deflects said negative ion beam onto said first apertured member so that only mass-14 particles having the known energy pass through said first aperture.

3. The apparatus of claim 1 wherein the mass analyzer comprises the following components:

a magnetic deflector that deflects said negative ion beam onto an apertured member so that only mass-14 particles having the known energy pass through said aperture;

an electric deflector that deflects said mass-14 particles passing through said aperture and directs them onto said first apertured member so that only mass-14 particles having the known energy pass through said first aperture.

4. The apparatus of claim 1 wherein the mass analyzer comprises the following components:

a magnetic deflector that deflects said negative ion beam onto an apertured member so that only mass-14 particles having the known energy pass through said aperture;

an electric deflector that deflects said mass-14 particles passing through said aperture and directs them onto said first apertured member so that only mass-14 particles having the known energy pass through said first aperture, a crossed electric and magnetic field arranged as a Wien velocity filter which directs said mass-14 particles into said first high voltage acceleration tube along said first acceleration axis and deflects away from said axis any residual backgrounds in said mass-14 negative ion beam which do not have a specified velocity.

5. The apparatus of claims 1, 2, 3 or 4 including a Faraday cup which collects carbon-12 ions having the said known energy which are deflected by said first magnetic deflector.

6. The apparatus of claim 5 including an electrostatic deflector which further deflects said carbon-12 ions before collection in said Faraday cup.

7. The apparatus of claims 1, 2, 3 or 4 wherein said foil stripper comprises multiple separated foils.

8. The apparatus of claims 1, 2, 3 or 4 wherein said 180° electrostatic deflecting field is formed between two metal conductors each having spherical shape and a common center.

9. The apparatus of claims 1, 2, 3, or 4 wherein said 180° electrostatic deflecting field is formed between two metal conductors each having cylindrical shape and a common line of centers.

10. The apparatus of claims 1, 2, 3 or 4 wherein the detector has the capability of measuring for individual particles the particle kinetic energy.

11. The apparatus of claims 1, 2, 3 or 4 wherein the detector has the capability of measuring for individual particles the rate of energy loss.

12. The apparatus of claims 1, 2, 3 or 4 wherein the detector includes a magnetic field deflection so that only mass-14 particles arrive at the sensitive region of the detector.

13. The apparatus of claims 1, 2, 3 or 4 wherein the detector includes a time-of-flight detector adapted to measure the velocity of the said particles having an energy of about 3E.

* * * * *